United States Patent [19]

Varma

[11] 4,361,559

[45] Nov. 30, 1982

[54] ANTIINFLAMMATORY 17,17-BIS (SUBSTITUTED THIO) ANDROSTENES

[75] Inventor: Ravi K. Varma, Belle Mead, N.J.

[73] Assignee: E. R. Squibb & Sons, Inc., Princeton, N.J.

[21] Appl. No.: 294,680

[22] Filed: Aug. 20, 1981

[51] Int. Cl.³ .............................................. A61K 31/56
[52] U.S. Cl. .................................... 424/243; 424/242; 260/397.45; 260/397.3
[58] Field of Search ..................................... 260/397.45

[56] References Cited

U.S. PATENT DOCUMENTS

| | | | |
|---|---|---|---|
| 4,091,036 | 5/1978 | Varma | 260/397.45 |
| 4,094,840 | 6/1978 | Varma | 260/397.45 |
| 4,133,811 | 1/1979 | Varma | 260/397.45 |
| 4,146,538 | 3/1979 | Varma et al. | 260/397.45 |

Primary Examiner—Elbert L. Roberts
Attorney, Agent, or Firm—Lawrence S. Levinson; Donald J. Barrack

[57] ABSTRACT

3-Ketoandrostenes having in the 17-position the substituents $R_1$—S— and $R_2$—S— wherein $R_1$ and $R_2$ are the same or different and each is alkyl, cycloalkyl or aryl, have antiinflammatory activity.

24 Claims, No Drawings

ANTIINFLAMMATORY 17,17-BIS (SUBSTITUTED THIO) ANDROSTENES

BACKGROUND OF THE INVENTION

U.S. Pat. Nos. 4,091,036, issued May 23, 1978, 4,094,840, issued June 13, 1978, 4,133,811, issued Jan. 9, 1979, and 4,146,538, issued Mar. 27, 1979, each discloses androstene intermediates wherein the D-ring has the formula

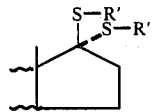

wherein R' is alkyl or aryl, and both R' groups are the same.

BRIEF DESCRIPTION OF THE INVENTION

Steroidal 17,17-bis(substituted thio) androstenes have been found to possess useful antiinflammatory activity.

This invention is directed to the treatment of inflammatory conditions in mammalian hosts by the topical administration of a 3-ketoandrostene having in the 17-position the substituents $R_1$-S- and $R_2$-S- wherein $R_1$ and $R_2$ are the same or different and each is alkyl, cycloalkyl or aryl.

Those 3-ketoandrostenes having in the 17-position the substituents $R_1$-S- and $R_2$-S- wherein $R_1$ and $R_2$ are different groups and each is alkyl, cycloalkyl or aryl are novel steroids, and as such, form an integral part of this invention.

A novel process for preparing 3-ketoandrostenes having in the 17-position the substituents $R_1$-S- and $R_2$-S- wherein $R_1$ and $R_2$ are the same is also disclosed herein and forms an integral part of this invention.

Exemplary of the above-described antiinflammatory 3-ketoandrostenes are those steroids having the formula

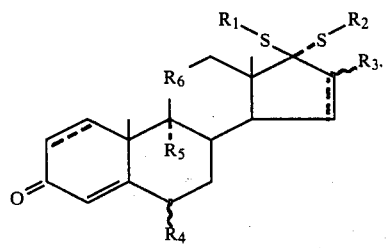

In formula I, and throughout the specification, the symbols are as defined below.

$R_1$ and $R_2$ are the same or different and each is alkyl, cycloalkyl or aryl;

$R_3$ is hydrogen, hydroxy, alkoxy, aryloxy, alkylthio, arylthio,

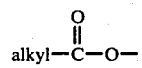

or halogen;

$R_4$ is hydrogen, methyl, hydroxy,

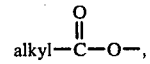

or halogen;

$R_5$ is hydrogen or halogen; and $R_6$ is carbonyl or $\beta$-hydroxymethylene. A broken line in the 1,2-, 6,7- and 15,16-position of a structural formula in this specification indicates the optional presence of ethylenic unsaturation.

The term "aryl", as used throughout the specification either individually or as part of a larger group, refers to phenyl or phenyl substituted with one or two alkyl, alkoxy or halogen groups.

The term "halogen", as used throughout the specification either individually or as part of a larger group, refers to fluorine, chlorine, bromine and iodine.

The terms "alkyl" and "alkoxy", as used throughout the specification either individually or as part of a larger group, refer to groups having 1 to 12 carbon atoms.

The term "cycloalkyl", as used throughout the specification, either individually or as part of larger group, refer to groups having 3, 4, 5, 6 or 7 carbon atoms.

The term "androstene", as used throughout the specification, refers to androstanes having ethylenic unsaturation in one or more positions. Exemplary of androstenes specifically contemplated are $\Delta^4$-androstenes, $\Delta^{1,4}$-androstadienes, $\Delta^{4,6}$-androstadienes, $\Delta^{1,4,6}$-androstatrienes, $\Delta^{1,4,15}$-androstatrienes, $\Delta^{4,6,15}$-androstatrienes and $\Delta^{1,4,6,15}$-androstatetraenes.

As set forth above, the 3-ketoandrostenes having in the 17-position the substituents $R_1$-S- and $R_2$-S- wherein $R_1$ and $R_2$ are different groups are novel steroids that form an integral part of this invention.

The compounds of formula I wherein $R_1$ and $R_2$ are the same and $R_3$ is hydroxy, alkoxy, aryloxy, alkylthio, arylthio,

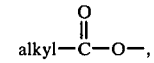

or halogen are also novel compounds that form an integral part of this invention.

DETAILED DESCRIPTION OF THE INVENTION

3-Ketoandrostenes having in the 17-position the substituents $R_1$-S- and $R_2$-S- are topical antiinflammatory agents that can be used to treat skin conditions such as dermatitis, psoriasis, sunburn, eczema, neurodermatitis, or anogenital pruritus, and in inhalation therapy for topical treatment of allergy and asthma.

For the treatment of skin conditions, the steroids useful in the method of this invention may be administered in a conventional pharmaceutical carrier in the form of a cream, ointment, lotion or the like. The steroids will preferably be used in the range of 0.01 to 5.0% by weight of the vehicle, preferably 0.05 to 2.0% by weight of the vehicle.

For the topical treatment of allergy and asthma the steroids useful in the method of this invention may be administered in the conventional manner, e.g., as solid medicament which has been atomized. U.S. Pat. Nos. 3,948,264 and 4,147,166 are exemplary of the literature which describes devices that can be used to administer solid medicaments for inhalation therapy.

The preparation of the 3-keto-17,17-bis(substituted thio)androstenes of this invention is described below with specific reference to the steroid of formula I. The practitioner of this invention will appreciate, however, that the methodology described is of general applicability.

The steroids of formula I can be prepared utilizing androstenes having the formula

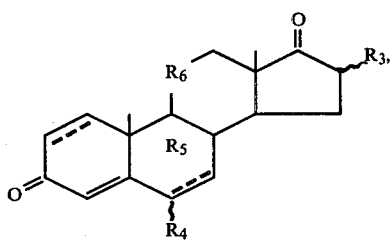

II as starting materials.

Reaction of an androstene of formula II with a thiol having the formula $R_1$-SH  III in the presence of a Lewis acid (e.g., boron trifluoride etherate), yields a product having the formula

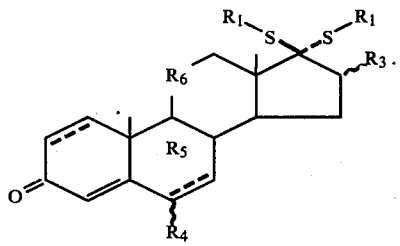

IV

The reaction can be run in an organic solvent (e.g., a halogenated hydrocarbon), or a mixture of organic solvents. The use of glacial acetic acid as the sole solvent, or in admixture with other solvents, improves yields. Reaction conditions are not critical and the reaction can be conveniently run at room temperature, preferably in an inert atmosphere (e.g., argon or nitrogen). Better yields can be obtained with relatively short reaction times (less than 1 hour).

It has been found that the yields of a reaction of a steroid of formula II with a thiol of formula III can be improved by adding a small amount of a dimethylformamide dialkyl acetal (preferably dimethylformamide dimethyl acetal). The use of such an agent improves both the yield and rate of the reaction, and tends to suppress the reaction of the thiol with the A-ring double bond and ketone functions. This improved process of making the compound of formula IV forms an integral part of this invention.

To prepare the steroids of formula I wherein $R_1$ and $R_2$ are different, an androstene of formula IV is first converted to the corresponding androstene having the formula

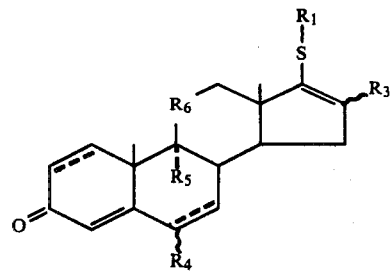

V by simply heating the steroid, either neat or in an inert solvent (e.g., diethylbenzene or dichlorobenzene).

Alternatively, compounds of formula V, wherein $R_3$ is chlorine, bromine, alkylthio, or arylthio can be prepared from the corresponding steroid of formula V wherein $R_3$ is hydrogen; i.e., a steroid having the formula

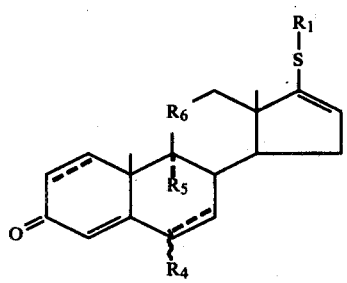

VI

Utilizing the procedure described in U.S. patent application Ser. No. 135,823, filed Mar. 31, 1980, a steroid of formula V wherein $R_3$ is chlorine or bromine can be obtained by reacting a steroid of formula VI with the appropriate N-halosuccinimide, or with chlorine or bromine, preferably in a halogenated hydrocarbon solvent. Steroids of formula V wherein $R_3$ is alkylthio or arylthio can be obtained by reacting the corresponding steroid of formula VI with an alkyl or aryl sulfenyl halide, preferably in a halogenated hydrocarbon solvent.

Reaction of a steroid of formula V with a thiol having the formula $R_2$-SH  VII yields the corresponding steroid having the formula

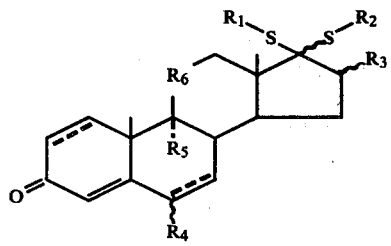

VIII as a mixture of isomers. The reaction is run in the presence of a Lewis acid (e.g., boron trifluoride etherate) and will preferably be run at a reduced temperature (i.e., about $-20°$ C. to $-100°$ C.). When the reaction is run at a reduced temperature (i.e., about $-20°$ C. to $-100°$ C.), it is stereospecific, and yields a steroid having the formula

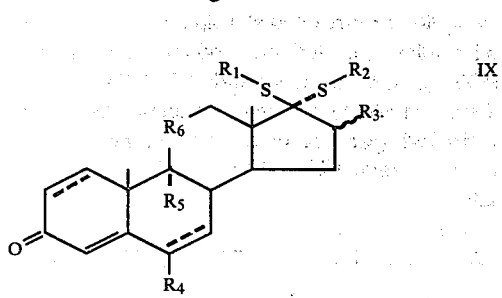 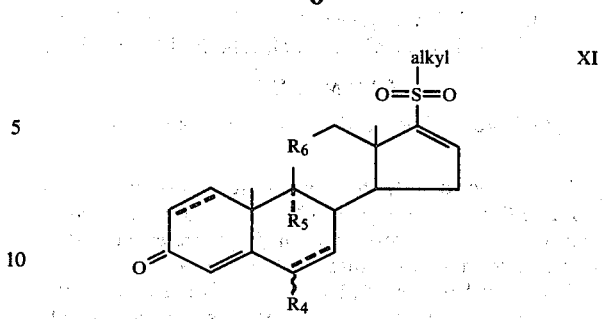

The 11-hydroxyl group of a steroid of formula V may be protected before its reaction with a thiol of formula VII. An exemplary family of protecting groups is the acyl family, e.g., alkanoyl groups such as acetyl. Means for protection and deprotection of the 11-hydroxyl group are well-known in the art. When preparing a compound of formula VIII or IX from an androstene-3,17-dione of formula II, it may be desirable to protect the 11-hydroxyl group as the first step of the synthesis.

The steroids of formula I having ethylenic unsaturation in the 15,16-position can be prepared from the corresponding 16-haloandrostene. Refluxing the 16-haloandrostene in an organic solvent in the presence of 1,5-diazabicyclo (5.4.0) undec-5-ene yields the desired 15,16-unsaturation. Alternatively, the steroids of formula I having ethylenic unsaturation in the 15,16-position can be prepared from the corresponding 16-hydroxyandrostene. Dehydrating the 16-hydroxyandrostene, using a dehydrating agent such as thionyl chloride, yields the desired 15,16-unsaturation.

The starting androstenes of formula II can be prepared by treating the corresponding pregnene having the formula

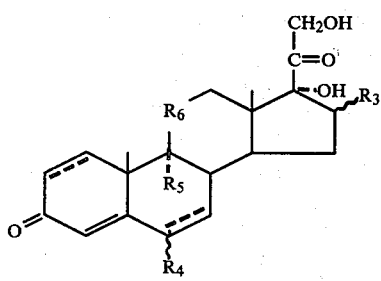

with sodium bismuthate in the presence of an acid, such as acetic acid.

Alternatively, the starting androstenes of formula II wherein R₃ is hydroxy or

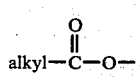

can be prepared by oxidation of the corresponding androstene having the formula with potassium permanganate in the presence of formic acid. The oxidation reaction yields the corresponding 16α-hydroxyandrostene-3,17-dione. This can be acylated using art-recognized procedures to yield the corresponding 17-alkanoyloxy derivative.

The following examples are specific embodiments of this invention.

EXAMPLE 1

(11β,16α)-9-Fluoro-11,16-dihydroxy-17,17-bis-(methylthio)androsta-1,4-dien-3-one (A)

9-Fluoro-11β,16α-dihydroxyandrosta-1,4-diene-3,17-dione

A solution of 9-fluoro-11β-hydroxy-17-(methylsulfonyl)androsta-1,4,16-triene-3-one (760 mg) in purified acetone (250 ml) is stirred in a bath at −3° to 0° C. and 3.0 ml of 10% (w/v) formic acid is added followed dropwise by a solution of potassium permanganate (540 mg) in purified acetone (250 ml). After 2.0 hours a few drops of 30% hydrogen peroxide are added to decompose any excess permanganate. The mixture is then filtered through a bed of anhydrous magnesium sulfate which is subsequently washed with small amounts of acetone. The filtrate and the washings are combined and concentrated in vacuo. The concentrate is diluted with water (500 ml) and extracted with chloroform. The chloroform extracts are combined, washed with water, dried (MgSO₄ anhydrous) and evaporated to afford the title compound (550 mg) as a crystalline solid. Crystallization of this from acetonehexane gives the analytical specimen, melting point 227°–228° C., with consistent spectral data.

(B)

(11β,16α)-9-Fluoro-11,16-dihydroxy-17,17-bis-(methylthio)androsta)-1,4-dien-3-one To an ice-cold solution of 9-fluoro-11β,16α-dihydroxyandrosta-1,4-diene-3,17-dione (300 mg) in a mixture of dichloromethane (6.0 ml) and acetic acid (6.0 ml) containing methanethiol (0.3 ml) is added boron trifluoride etherate (0.3 ml). The solution is then stirred at room temperature for 35 minutes. It is then poured into water and extracted with chloroform. The chloroform solution is washed with a dilute sodium bicarbonate solution and water, dried (MgSO₄ anhydrous) and is evaporated to afford a glassy solid. The solid is chromatographed on a column of silica gel (10 g) eluting the column with chloroform and chloroform-ethyl acetate mixtures to afford the homogeneous title compound as a solid (170 mg). One recrystallization of this from acetone-hexane and drying (100° C., 0.3 mm of Hg, 10 hours) gives the analytical specimen (143 mg) melting point 261°–262° C., dec. with consistent spectral data.

Anal. Calcd. for $C_{21}H_{29}FO_3S_2$: C, 61.13; H, 7.08; F, 4.61; S, 15.54; Found: C, 61.29; H, 7.14; F, 4.60; S, 15.39.

EXAMPLE 2

17,17-Bis(ethylthio)-11β-hydroxyandrosta-1,4-dien-3-one

A solution of 11β-hydroxyandrosta-1,4-diene-3,17-dione (1.0 g) in acetic acid (25 ml) containing ethanethiol (1.5 ml) and boron trifluoride etherate (2.0 ml) is stirred at room temperature for 45 minutes. The mixture is then added to water (200 ml) and is extracted with chloroform. The chloroform extracts are combined, washed with a saturated sodium bicarbonate solution and water dried (MgSO₄ anhydrous) and evaporated in vacuo at a gummy residue. The residue is chromatographed on a column of silica gel (30 g) eluting successively with chloroform-hexane (4:1), chloroform and chloroform-ethyl acetate (9:1 and 4:1) to isolate respectively the overreacted steroid (about 100 mg), the homogeneous (tlc) title compound (1.2 g) and unreacted starting steroid (about 75 mg). One crystallization of the 1.2 g of solid from ethyl acetate-hexane affords flakes of the analytical specimen of the title compound (800 mg) melting point 163°–165° C. with consistent spectral data, after drying at 100° C. at 0.3 mm of Hg for 7 hours.

Anal. Calcd. for $C_{23}H_{34}O_2S_2$: C, 67.93; H, 8.43; S, 15.77; Found: C, 67.84; H, 8.45; S, 15.69.

EXAMPLE 3

(11β)-9-Fluoro-11-hydroxy-17,17-bis(propylthio)-androsta-1,4-dien-3-one

Boron trifluoride etherate (3.58 g) is added to a solution of 9-fluoro-11β-hydroxyandrosta-1,4-diene-3,17-dione (1.5 g), n-propanethiol (1.77 g) and dimethylformamidedimethylacetal (1.52 g) in glacial acetic acid (35 ml). After 2 hours, the reaction mixture is poured into water (300 ml) and the products are extracted into chloroform. The chloroform extracts are combined, washed with water, a dilute NaHCO₃ solution and water, dried (MgSO₄ anhydrous) and evaporated to afford the product as a solid (1.8 g). This is chromatographed on a column of silica gel (25 g) eluting with chloroform-hexane (4:1), chloroform and chloroform-ethyl acetate (95:5 and 9:1) to isolate the title compound (1.20 g) and unreacted starting material (400 mg). Two recrystallizations of the 1.2 g material from ethyl acetate-hexane and drying (105° C., 0.3 mm of Hg, 6.0 hours) gives the analytical specimen (900 mg) melting point 235°–237° C., with constant spectral data.

Anal. for $C_{25}H_{37}FO_2S_2$; Calc'd: C, 66.33; H, 8.22; S, 14.16; F, 4.20; Found: C, 66.34; H, 8.29; S, 14.06; F, 4.29.

EXAMPLE 4

(11β)-17,17-Bis(butylthio)-9-fluoro-11-hydroxyandrosta-1,4-dien-3-one

To a solution of 9-fluoro-11β-hydroxyandrosta-1,4-diene-3,17-dione (4.2 g) in glacial acetic acid (120 ml) containing n-butanethiol (5.0 ml) is added boron trifluoride etherate (2.5 ml). A blue color develops after about 1.0 hour. The blue reaction mixture is poured into water (700 ml) and extracted with chloroform. The chloroform extracts are combined, washed with a saturated sodium bicarbonate solution and water, dried (MgSO₄, anhydrous) and evaporated to a gummy residue. This is chromatographed over silica gel (70 g), eluting the column with chloroform-hexane (8:2), chloroform and chloroform-ethyl acetate (9:1 and 8:2) to isolate successively the over-reacted steroidal material contaminated with other thiol-derived products, the title compound (400 mg) and starting steroid (2.5 g). Two recrystallizations of the 400 mg from ethyl acetate-hexane gives the analytical specimen of the title compound (125 mg), melting point 160°–162° C., with consistent spectral data.

Anal. Calcd. for $C_{27}H_{41}FO_2S_1$: C, 67.45; H, 8.59; F, 3.95; S, 13.34; Found: C, 67.37; H, 8.61; F, 3.86; S, 13.29.

EXAMPLE 5

(11β,16α)-17,17-Bis(ethylthio)-9-fluoro-11-hydroxy-16-methoxyandrosta-1,4-dien-3-one (A)

9-Fluoro-11β-hydroxy-16α-methoxyandrosta-1,4-dien-3,17-one

9-Fluoro-11β,17-21-trihydroxy-16α-methoxypregna-1,4-diene-3,20-dione (4.0 g) is dissolved in 50% acetic acid (300 ml) by warming. The solution is cooled to room temperature, sodium bismuthate (25 g) is added and the mixture is stirred at 55° C. (oil bath temperature) for 24 hours. The resulting mixture is filtered through a bed of Hyflo and washed with a small amount of warm 50% acetic acid. The filtrate is concentrated to 50 ml in vacuo, diluted with 200 ml of 20% hydrochloric acid and extracted with chloroform. The chloroform solution is washed with water, dried over anhydrous Na₂SO₄ and evaporated in vacuo to give a foam (3.0 g). This is dissolved in chloroform and chromatographed on a 30 g-silica gel column, eluting successively with chloroform and chloroform-ethyl acetate (95:5, 9:1 and 8:2) to give 1.4 g of a slightly impure title compound. This is rinsed with chloroform-hexane (1:1) to give 1.0 g of thin-layer chromatography (tlc)-homogeneous solid, melting point 204°–210° C. with consistent spectral data.

(B)

(11β,16α)-17,17-Bis(ethylthio)-9-fluoro-11-hydroxy-16-methoxyandrosta-1,4-dien-3-one A solution of 1.0 g of 9-fluoro-11β-hydroxy-16α-methoxyandrosta-1,4-dien-3,17-dione, 1.06 ml of ethanethiol, 1.78 ml of boron trifluoride etherate and 853 mg of N,N-dimethylformamide dimethyl acetal in 28 ml of glacial acetic acid is stirred at room temperature under nitrogen for 1.5 hour. The resulting solution is diluted with chloroform, washed with water, saturated NaHCO₃ solution and water, dried over anhydrous Na₂SO₄ and evaporated in vacuo to give a foam. This is dissolved in chloroform-hexane (9:1) and chromatographed on a 35 g-silica gel column, eluting successively with chloroform-hexane (9:1), chloroform, chloroform-ethyl acetate (95:5) and chloroform-methanol (9:1) to give an over-reacted steroidal product (130 mg), 9-fluoro-11β-hyroxy-16α-methoxyandrosta-1,4-diene-3,20-dione (230 mg) and title compound (510 mg). The title compound is recrystallized from acetone-hexane to give 385 mg of an analytical specimen, melting point 234°–239° C., with consistent spectral data.

Anal. Calcd. for $C_{24}H_{35}FO_3S_2$: C, 63.40; H, 7.76; F, 4.18; S, 14.11; Found: C, 63.26; H, 7.78; F, 4.21; S, 14.00.

EXAMPLE 6

9-Fluoro-11β-hydroxy-17,17-bis(phenylthio)androsta-1,4-dien-3-one

A solution of 9.0 g of 9-fluoro-11β-hydroxyandrosta-1,4-diene-4,17-dione in 50 ml of dichloromethane and 50 ml of glacial acetic acid is stirred with 18.68 g of thiophenol and 7.5 ml of boron trifluoride etherate at room temperature under nitrogen. After 50 minutes the solution is diluted with 350 ml of chloroform. The chloroform solution is washed with water, saturated NaHCO$_3$ solution and water, dried over anhydrous Na$_2$SO$_4$ and evaporated in vacuo to give 11.6 g of an oil. This is dissolved in 1:3 hexane-chloroform and chromatographed on a 200 g-silica gel column. Elution with 1:3 hexane-chloroform and chloroform gives 3.5 g of a homogeneous material. Crystallization from chloroform-methanol gives 2.0 g of the title compound, melting point 249°–250° C., dec. with consistent spectral data.

Anal. Calcd. for C$_{31}$H$_{33}$FO$_2$S$_2$: C, 71.50; H, 6.39; F, 3.65; S, 12.32; Found: C, 71.66; H, 6.49; F, 3.92; S, 12.41.

EXAMPLE 7

9-Fluoro-11β-hydroxy-17,17-bis(methylthio)androsta-1,4-dien-3-one

A solution of 9-fluoro-11β-hydroxyandrosta-1,4-diene-3,20-dione (2.0 g) in glacial acetic acid (25 ml) is mixed at room temperature with a solution of methanethiol (2.4 g) in dichloromethane (16 ml) and boron trifluoride etherate (0.5 ml). After 1.5 hours, the mixture is poured into water and diluted with chloroform. The organic layer is then separated, washed with a dilute sodium bicarbonate solution and water, dried (MgSO$_4$ anhydrous) and evaporated in vacuo. The residue is absorbed on a column of silica gel (50 g). Elution of the column with chloroform removes the non-steroidal impurities and a product resulting from thiol addition to the A-ring. Subsequent elution with chloroform affords the homogeneous product as a solid (957 mg). Elution with chloroform-ethyl acetate (95:5) affords the unreacted steroid (345 mg). A specimen of the 957 mg of solid is crystallized from chloroform-methanol to afford the analytical specimen of product, melting point 305° C., dec, with consistant spectral data.

Anal. Calcd. for C$_{21}$H$_{29}$FO$_2$S$_2$: C, 63.60; H, 7.37; F, 4.79; S, 16.17; Found: C, 63.48; H, 7.21; F, 4.95; S, 16.21.

EXAMPLE 8

17,17-Bis(ethylthio)-9-fluoro-11β-hydroxyandrosta-1,4-dien-3-one

A solution of 9.5 g of 9-fluoro-11β-hydroxyandrosta-1,4-diene-3,17-dione in 50 ml of dichloromethane and 50 ml of glacial acetic acid is stirred with 11.2 g of ethanethiol and 7.5 ml of boron trifluoride etherate at room temperature under nitrogen. After 1.5 hours the solution is diluted with 350 ml of chloroform. The chloroform solution is washed with water, saturated NaHCO$_3$ solution and water, dried over anhydrous Na$_2$SO$_4$ and evaporated in vacuo to give 11 g of a foamy solid. This is dissolved in hexane-chloroform (2:1) and chromatographed on a 200 g-silica gel column. Elution with hexane-chloroform (2:1 and 1:1) gives 2.1 g of a homogeneous material. Crystallization from acetone-hexane gives 1.05 g of the title compound, melting point 276°–277° C., dec., with consistent spectral data.

Anal. Calcd. for C$_{23}$H$_{33}$FO$_2$S$_2$: C, 65.05; H, 7.83; F, 4.47; S, 15.10; Found: C, 65.31; H, 7.80; F, 4.71; S, 15.01.

EXAMPLE 9

9-Fluoro-11β-hydroxy-17,17-bis[(4-methoxyphenyl)thio]androsta-1,4-dien-3-one To a solution of 9-fluoro-11β-hydroxyandrosta-1,4-diene-3,17-dione (3.18 g) in a mixture of dry dichloromethane (40 ml) and glacial acetic acid (40 ml) containing p-methoxybenzenethiol (5.6 g) is added boron trifluoride etherate (3.0 ml) and the resulting solution is stirred for 1.5 hours. It is then poured into water (500 ml) and extracted with chloroform. The chloroform extracts are combined, washed with saturated sodium bicarbonate solution and water, dried (MgSO$_4$) and concentrated in vacuo to a syrupy residue. This is absorbed on a column of silica gel (50 g) made up in chloroform-hexane (1:1) and the column is eluted successively with chloroform-hexane (1:1), chloroform and chloroform-ethyl acetate mixtures (95:5 and 90:10) to elute successively p-methoxybenzenethiol contaminated with some steroidal impurities, the title compound (3.0 g), a small amount of an undentified compound and unreacted starting material (1.0 g). The 3.0 g of material is refluxed with ethyl acetate (30 ml), cooled and filtered to leave the analytical specimen (dried at 0.3 mm of Hg, 100° C., 18 hours) of the title compound (2.8 g), melting point 209°–211° C., with consistent spectral data.

Anal. for C$_{33}$H$_{37}$FO$_4$S$_2$: Calcd: C, 68.25; H, 6.42; F, 3.27; S, 11.04; Found: C, 68.46; H, 6.63; F, 3.25; S, 11.20.

EXAMPLE 10

17-(Ethylthio)-9-fluoro-11β-hydroxy-17-(methylthio)androsta-1,4-dien-3-one (A)

11β-Acetyloxy-9-fluoroandrosta-1,4-diene-3,17-dione

A solution of 9-fluoro-11β-hydroxyandrosta-1,4-diene-3,17-dione (5.0 g) in a mixture of acetic acid (60 ml) and acetic anhydride (60 ml) containing p-toluenesulfonic acid (2.5 g) is maintained at room temperature for eighteen hours. Sodium acetate (2.5 g) is added and the mixture is concentrated in vacuo at 35°–40° C. The residue is diluted with water (150 ml) and the solid that separates is isolated by filtration, washed with water and dried in vacuo to afford the title compound as a solid (5.0 g) with consistent spectral data. An examination (silica gel, chloroform: ethyl acetate, 95:5) reveals the presence of a small amount of starting steroid as the only significant impurity. This material is used without purification in the next step. A specimen crystallized from acetone-hexane melts at 173°–174° C.

(B)

11β-Acetyloxy-17,17-bis(methylthio)-9-fluoroandrosta-1,4-diene-3-one

To a solution of 11β-acetyloxy-9-fluoroandrosta-1,4-diene-3-one (5.0 g) in a mixture of acetic acid (25 ml) and dichloromethane (25 ml) containing methanethiol (2.5 ml) is added distilled boron trifluoride etherate (0.5 ml) and the mixture is stirred for one hour. It is then added to water (150 ml) and is extracted with chloroform. The chloroform solution is washed with water, saturated NaHCO$_3$ solution and water, dried (MgSO$_4$ anhydrous) and evaporated. The residue is absorbed on a column of silica gel (30 g). Successive elutions of the column with chloroform-hexane (4:1), chloroform and chloroform-ethyl acetate (95:5 and 9:1) afford over-reacted steroid containing thiol-derived impurities (3.0 g), the title compound (1.7 g) and unreacted starting material. Crystallization of the 1.7 g material from acetone-hexane gives 1.2 g of material, melting point 220°–222° C., with consistent spectral data.

(C)
11β-Acetyloxy-9-fluoro-17-(methylthio)-androsta-1,4,16-trien-3-one

11β-Acetyloxy-17,17-bis(methylthio)-9-fluoroandrosta-1,4-diene-3-one (1.1 g) is suspended in dry diethylbenzene (30 ml). After refluxing for twenty minutes, the solution is cooled, poured on a column of silica gel (15 g) and the column is eluted successively with chloroform-hexane (7:3), chloroform and chloroform-ethyl acetate (95:5) to isolate the title compound (900 mg) and 11β-acetyloxy-9-fluoroandrosta-1,4-diene-3,17-dione (120 mg). Crystallization of the 900 mg of material from ethyl acetate-hexane gives 800 mg of material, melting point 192°–194° C., with consistent spectral data.

(D)
11β-Acetyloxy-17-(ethylthio)-9-fluoro-17-(methylthio)androsta-1,4-diene-3-one To a solution of 11β-acetyloxy-9-fluoro-17-(methylthio)androsta-1,4-diene-3-one (632 mg) in dry dichloromethane (20 ml) containing dry ethanethiol (0.6 ml) is added boron trifluoride etherate (0.25 ml). After one hour, the mixture is added to a NaHCO3 solution and extracted with chloroform. The chloroform solution is washed with water, dried (MgSO4 anhydrous), and evaporated to afford the title compound (620 mg) contaminated with a small amount of 11β-acetyloxy-9-fluoroandrosta-1,4-diene-3,17-dione. This material is used in the next step without further purification. A specimen crystallized from acetone-hexane shows melting point 140°–142° C. and a consistent nmr spectrum.

(E)
17-(Ethylthio)-9-fluoro-11β-hydroxy-17-(methylthio)androsta-1,4-diene-3-one

A solution of 11β-acetyloxy-17-(ethylthio)-9-fluoro-17-(methylthio)androsta-1,4-diene-3-one (620 mg) in a mixture of methanol (20 ml) and tetrahydrofuran (10 ml) is stirred under nitrogen with 3 M aqueous sodium hydroxide (1.5 ml). After eighteen hours, a slight excess of acetic acid is added. The mixture is concentrated in vacuo, diluted with water and extracted with chloroform. The chloroform solution is washed with water, dried, evaporated and chromatographed over a column of silica gel (10 g) eluting the column successively with chloroform-hexane (4:1), chloroform and chloroform-ethyl acetate (95:5) to isolate the title compound (550 mg). Crystallization of this from ethyl acetate-hexane and drying (110° C., 0.3 mm of Hg, 7 hours) gives the analytical specimen, melting point 275° C., dec. (contracts from approximately 200° C., discoloration starts from approximately 220° C. and becomes deeper until spontaneous melting at 275° C. with decomposition) with consistent spectral data. The nmr spectrum shows that this is an essentially 1:1 mixture of the two 17-stereoisomers.

Anal. Calcd. for $C_{22}H_{31}FO_2S_2$: C, 64.35; H, 7.61; F, 4.63; S, 15.62; Found: C, 64.16; H, 7.69; F, 4.59; S, 15.49.

EXAMPLE 11
17-(Ethylthio)-9-fluoro-11β-hydroxy-17-(phenylthio)androsta-1,4-dien-3-one, isomer A (A)
11β-Acetyloxy-9-fluoroandrosta-1,4-diene-3,17-dione A solution of 20 g of 9-fluoro-11β-hydroxyandrosta-1,4-diene-3,17-dione, 120 ml of glacial acetic acid, 120 ml of acetic anhydride and 5 g of p-toluenesulfonic acid is stirred at room temperature under nitrogen for 24 hours. The resulting solution is quenched with 5 g of sodium acetate. The solvent is partially removed in vacuo at 35°–40° C. and the resultant slurry is diluted with chloroform. The chloroform solution is washed with water, saturated sodium bicarbonate and water, dried over anhydrous $Na_2SO_4$ and evaporated in vacuo to give the title compound. This is crystallized from ethyl acetate-hexane to give 20 g of the title compound melting point 171°–174° C., with consistent spectral data.

(B)
11β-Acetyloxy-17,17-bis(ethylthio)-9-fluoroandrosta-1,4-dien-3-one

A solution of 20 g (55.5 mmole) of 11β-acetyloxy-9-fluoroandrosta-1,4-diene-3,17-dione in 75 ml of dry dichloromethane and 75 ml of glacial acetic acid is stirred with 10 ml of ethanethiol and 2 ml of boron trifluoride etherate at room temperature under nitrogen. After 2.0 hours the resulting solution is diluted with dichloromethane, washed with water, saturated sodium bicarbonate and water, dried over anhydrous $Na_2SO_4$ and evaporated in vacuo. The gummy residue is dissolved in 1:1 chloroform-hexane and chromatographed on a 150 g-silica gel column, eluting successively with chloroform-hexane (1:1, 6:4 and 7:3), chloroform, chloroform-ethyl acetate (5:95 and 1:9) and methanol-chloroform (1:9) to give 9.5 g of unreacted 11β-acetyloxy-9-fluoroandrosta-1,4-diene-3,17-dione, 8.2 g of over-reacted steroidal product and 5.2 g of the title compound, melting point 246°–250° C., with consistent spectral data.

(C)
11β-Acetyloxy-17-(ethylthio)-9-fluoroandrosta-1,4,16-trien-3-one

A suspension of 5.2 g of 11β-acetyloxy-17,17-bis(ethylthio)-9-fluoroandrosta-1,4-dien-3-one in 85 ml of dry diethylbenzene is stirred at 180° C. (oil bath temperature) for 1.0 hour; the suspension gradually becomes a homogeneous solution during the heating. The resulting solution is cooled to 0° C. and the solid that precipitates is filtered and dried in vacuo to give 3.6 g of the title compound, melting point 211°–215° C., with consistent spectral data.

The filtrate is chromatographed on a 30 g-silica gel column, eluting successively with chloroform-hexane (1:1) and chloroform to give 0.4 g more of the title compound.

(D)
11β-Acetyloxy-17-(ethylthio)-9-fluoro-17-(phenylthio)androsta-1,4-dien-3-one A solution of 1.2 g (2.97 mmole) of 11β-acetyloxy-17-(ethylthio)-9-fluoroandrosta-1,4,16-trien-3-one, 18 ml of dry dichloromethane and 0.8 ml of thiophenol is cooled to −20° C. under nitrogen. Boron trifluoride etherate (0.6 ml) is then added. The solution is stirred at −10° to −20° C. for 2 hours under nitrogen. The resulting solution is diluted with dichloromethane, washed with saturated sodium bicarbonate and water, dried over anhydrous $Na_2SO_4$ and evaporated in vacuo to give a gum. This is dissolved in chloroform-hexane (1:1) and chromatographed on a 20 g-silica gel column, eluting successively with chloroform-hexane (1:1), chloroform, chloroform-ethyl acetate (95:5) and chloroform-methanol (9:1) to give 1.0 g of impure title compound. This is dissolved in the minimum amount of ethyl acetate and stood at room temperature for 2 days. The solid that precipitates is filtered to give 480 mg of title compound, melting point 152°–158° C., with consistent spectral data.

(E)
17-Ethylthio)-9-fluoro-11β-hydroxy-17-(phenylthio)androsta-1,4-dien-3-one, isomer A A stream of nitrogen is bubbled through a solution of 560 mg of 11β-acetyloxy-17-(ethylthio)-9-fluoro-17-(phenylthio)androsta-1,4-dien-3-one in a mixture of tetrahydrofuran (30 ml), methanol (15 ml) and water (1.0 ml) for 15 minutes; sodium hydroxide (12%, 1.2 ml) is then added. The solution is stirred at room temperature under nitrogen for 1.5 hour, acidified with acetic acid, and evaporated in vacuo to give a solid. This is rinsed with a small amount of water to give 480 mg of the title compound. Recrystallization from acetone-hexane gives 400 mg of an analytical specimen, melting point 272°–273° dec., with consistent spectral data.

Anal. Calcd. for $C_{27}H_{33}FO_2S_2$: C, 68.61; H, 7.04; F, 4.02; S, 13.57; Found: C, 68.37; H, 7.00; F, 4.08; S, 13.56.

EXAMPLE 12

17-(Ethylthio)-9-fluoro-11β-hydroxy-17-(phenylthio)-androsta-1,4-dien-3-one, isomer B (A)
11β-Acetyloxy-17,17-bis(phenylthio)-9-fluoroandrosta-1,4-dien-3-one A solution of 8.5 g of 11β-acetyloxy-9-fluoroandrosta-1,4-diene-3,17-dione (see example 10A) in 60 ml of dry dichloromethane and 60 ml of glacial acetic acid is stirred with 8.0 ml of thiophenol and 1.5 ml of boron trifluoride etherate at room temperature under nitrogen for 3.5 hours. The resulting solution is diluted with dichloromethane, washed with water, saturated sodium bicarbonate and water, dried over anhydrous $Na_2SO_4$ and evaporated in vacuo. The gummy residue is dissolved in 7:3 chloroform-hexane and chromatographed on a 100 g silica gel column, eluting successively with chloroform-hexane (7:3), chloroform, chloroform-ethyl acetate (9:1) and chloroform-methanol (9:1) to give 4.8 g of unreacted 11β-acetyloxy-9-fluoroandrosta-1,4-diene-3,17-dione, 3.0 g of over-reacted steroidal product and 1.5 g of the title compound, melting point 233°–235° C., with consistent spectral data.

(B)
11β-Acetyloxy-9-fluoro-17-(phenylthio)androsta-1,4,16-trien-3-one

A suspension of 1.5 g of 11β-acetyloxy-17,17-bis(phenylthio)-9-fluoroandrosta-1,4-dien-3-one in 25 ml of dry diethylbenzene is stirred at 185°–190° C. (oil bath temperature) for 1.0 hour. The suspension gradually becomes a homogeneous solution during the heating and the resulting solution is cooled to 0° C. The solid that precipitates is filtered and dried in vacuo to give 0.9 g of the title compound, melting point 228°–229° C., with consistent spectral data.

The filtrate is chromatographed on a 25 g-silica gel column, eluting successively with 1:1 chloroform-hexane and 1:9 chloroform-ethyl acetate to give 0.25 g more of the title compound.

(C)
11β-Acetyloxy-17-(ethylthio)-9-fluoro-17-(phenylthio)androsta-1,4-dien-3-one, Isomer B A solution of 1.0 g of 11β-acetyloxy-9-fluoro-17-(phenylthio)androsta-1,4,16-trien-3-one, 12 ml of dry dichloromethane and 0.5 ml of ethanethiol is cooled to −10° C. under nitrogen. Boron trifluoride etherate is then added. The solution is stirred at −10° C. under nitrogen for 2.5 hours. The resulting solution is diluted with dichloromethane, washed with saturated sodium bicarbonate and water, dried over anhydrous $Na_2SO_4$ and evaporated in vacuo to give a foamy solid. This is dissolved in chloroform and chromatographed on two precoated silica gel TLC plates (E. Merck, 20 cm×20 cm×2 mm, 1:4 ethyl acetate-chloroform for development) to give 800 mg of slightly impure title compound. This is crystallized from ethyl acetate-hexane to give 500 mg of title compound, melting point 145°–148° C., with consistent spectral data.

(D)
17-(Ethylthio)-9-fluoro-11β-hydroxy-17-(phenylthio)androsta-1,4-dien-3-one, isomer B A stream of nitrogen is bubbled through a solution of 545 mg of 11β-acetyloxy-17-(ethylthio)-9-fluoro-17-(phenylthio)androsta-1,4-dien-3-one in a mixture of tetrahydrofuran (30 ml), methanol (15 ml) and water (1.0 ml) for 15 minutes. Sodium hydroxide (12%, 1.2 ml) is then added. The solution is stirred at room temperature under nitrogen for 1.5 hours. The resulting solution is acidified with acetic acid and the solvent is evaporated in vacuo to give a solid. This is rinsed with a small amount of water and filtered. The solid is recrystallized from acetone-hexane to give 370 mg of an analytical specimen, melting point 263°–264° C., dec., with consistent spectral data.

Anal. Calcd. for $C_{27}H_{33}FO_2S_2$: C, 68.61; H, 7.04; F, 4.02; S, 13.57; Found: C, 68.73; H, 6.81; F, 4.04; S, 13.52.

EXAMPLE 13

17-(Butylthio)-17-(ethylthio)-9-fluoro-11β-hydroxyandrosta-1,4-dien-3-one (A)
11β-Acetyloxy-17-(butylthio)-17-(ethylthio)-9-fluoroandrosta-1,4-diene-3-one A solution of 11β-acetyloxy-17-(ethylthio)-9-fluoroandrosta-1,4,16-triene-3-one (700 mg; see example 11c) and n-butanethiol (271 mg) is cooled and stirred in a bath at −40° to −45° C. and distilled boron trifluoride etherate (0.3 ml) is added. After 2.0 hours at −40° to −45° C., the solution is gradually warmed to 10° C. in the course of 1.5 hours. The mixture is then diluted with dichloromethane, washed successively with a saturated sodium bicarbonate solution and brine, dried (MgSO₄ anh.) and is evaporated to afford the crude title compound. This material is chromatographed over a column of silica gel (20 g), eluting the column with chloroform-hexane mixtures (1:1, 1:4), chloroform and chloroform-ethyl acetate (95:5) to afford the title compound (700 mg). Examination of the nmr spectrum and tlc behavior shows that this material is contaminated with a significant amount of the starting steriod which is not readily separable from the more polar isomer of the product under the tlc systems examined. Partial separation of the two 17-isomers is achieved under these tlc conditions.

(B)
17-(Butylthio)-17-(ethylthio)-9-fluoro-11β-hydroxyandrosta-1,4-dien-3-one

11β-Acetyloxy-17-(butylthio)-17-(ethylthio)-9-fluoroandrosta-1,4-diene-3-one (925 mg) is dissolved in a mixture of methanol (20 ml) and tetrahydrofuran (20 ml). The solution is stirred, purged with nitrogen and 3.0 M sodium hydroxide (3.0 ml) is added. After 2 hours a slight excess of acetic acid is added and the mixture is then concentrated in vacuo. It is diluted with water (150 ml) and extracted with chloroform. The chloroform extract is washed with water, dried (MgSO₄ anh.) and evaporated to afford the title compound (870 mg). Examinations of the nmr spectrum and tlc behavior of this compound show the presence of some 17-(ethylthio)-9-fluoro-11β-hydroxyandrosta-1,4,16-triene-3-one and two 17-stereoisomers of the title compound. The material is applied on four 2.0 mm Merck silica gel plates and the plates are developed twice with chloroform-ethyl acetate (7:3). The products from the upper ⅓ and lower ⅔ of the broad band are isolated separately by extraction with chloroform-methanol (3:1) to afford respectively 340 and 527 mg of solids. One crystallization of the 340 mg of solid from ethyl acetate-hexane (1:1) and drying (100° C., 0.3 mm of Hg, 20 hours) gives the analytical specimen of the title compound (281 mg) melting point 118°–125° C. with consistent spectral data.

Anal. Calc'd for $C_{25}H_{37}FO_2S_2$: C, 66.33; H, 8.24; F, 4.20; S, 14.16; Found: C, 66.10; H, 8.19; F, 4.01; S, 13.98.

EXAMPLE 14

17α-(Ethylthio)-9-fluoro-11β-hydroxy-17-(methylthio)androsta-1,4-dien-3-one (A)
11β-Acetyloxy-17α-(ethylthio)-9-fluoro-11-hydroxy-17-(methylthio) androsta-1,4-diene-3-one A solution of 11β-acetyloxy-9-fluoro-17-(methylthio)androsta-1,4,16-triene-3-one (2.1 g), in dry dichloromethane (45 ml) containing dry ethanethiol (1.5 ml) is cooled in a bath at about −40° C. (acetonitrile-dry ice bath) and boron trifluoride etherate (1.5 ml) is added. After 2.0 hours at about −40° C. the reaction is quenched by the addition of a 10% sodium carbonate solution under vigorous stirring at the low temperature. The mixture is then warmed to room temperature, diluted with water and extracted with chloroform. The chloroform extracts are combined, washed with water, dried (MgSO₄ anhydrous) and evaporated to afford the title compound in quantitative yield (2.38 g). Crystallization of this solid from acetone-hexane affords the analytical specimen (1.8 g), melting point 170°–172° C. with consistent spectral data.

(B)
17α-(Ethylthio)-9-fluoro-11β-hydroxy-17-(methylthio)androsta-1,4-dien-3-one

A solution of 11β-Acetyloxy-17α-(ethylthio)-9-fluoro-17-(methylthio)androsta-1,4-diene-3-one (1.85 g) in a mixture of methanol (15 ml) and tetrahydrofuran (15 ml) is stirred with 3 M sodium hydroxide solution (2.5 ml) for 1.5 hours. A moderate excess of acetic acid is then added and the mixture is concentrated in vacuo to a slurry (about 10 ml). This is diluted with ice-cold water, the precipitated solid is isolated by filtration, washed with water and dried to afford the title compound (1.62 g). Crystallization of this from acetone-hexane gives the analytical specimen (1.25 g) melting point 218°–220° C., with resolidification and remelting at 261°–265° C. with decomposition and discoloration.

Anal. Calc'd for $C_{22}H_{31}FO_2S_2$: C, 64.35; H, 7.61; F, 4.63; S, 15.62; Found: C, 64.57; H, 7.61; F, 4.85; S, 15.59.

EXAMPLE 15

17β-(Ethylthio)-9-fluoro-11β-hydroxy-17-(methylthio)androsta-1,4-dien-3-one (A)
11β-Acetyloxy-17β-ethylthio-9-fluoro-17-(methylthio)androsta-1,4-dien-3-one A solution of 1.01 g (2.5 mmole) of 11β-acetyloxy-17-(ethylthio)-9-fluoroandrosta-1,4,16-trien-3-one in 15 ml of dry dichloromethane and 3.4 ml of a solution of methyl mercaptan in dichloromethane (1.82 g in 10 ml of dry dichloromethane) is cooled to about −40° C. (acetonitrile-dry ice bath) under nitrogen; boron trifluoride etherate (0.7 ml) is then added. The solution is stirred at approximately −40° C. under nitrogen for 3 hours, quenched with a saturated sodium bicarbonate solution at −40° C. under vigorous stirring, diluted with chloroform, washed with water, dried over anhydrous Na₂SO₄ and evaporated in vacuo to give 1.0 g of the title compound, melting point 185°–186° C., with consistent spectral data.

(B)
17β-(Ethylthio)-9-fluoro-11β-hydroxy-17-(methylthio)androsta-1,4-dien-3-one

A stream of nitrogen is bubbled through a solution of 1.0 g of 11β-acetyloxy-17β-(ethylthio)-9-fluoro-17-(methylthio)-androsta-1,4-dien-3-one in a mixture of tetrahydrofuran (30 ml), methanol (25 ml) and water (2 ml) for 15 minutes. Sodium hydroxide (12%, 2.5 ml) is then added. The solution is stirred at room temperature under nitrogen for 2 hours, acidified with acetic acid and evaporated in vacuo to give a slurry. This is redissolved in chloroform, washed with water, dried over anhydrous Na₂SO₄ and evaporated in vacuo to give the title compound (855 mg). Crystallization from acetone-hexane gives 710 mg of the analytical specimen, melting point 258°–259° C. dec. with consistent spectral data.

Anal. Calc'd for $C_{22}H_{31}FO_2S_2$: C, 64.35, H, 7.61; F, 4.63; S, 15.62; Found: C, 64.57, H, 7.42; F, 4.79; S, 15.65.

EXAMPLE 16

11β-Hydroxy-17,17-bis(methylthio)androsta-1,4-dien-3-one

Boron trifluoride etherate (3.0 ml) is added to a solution of 11β-hydroxyandrosta-1,4-diene-3,17-dione (6.5 g) in glacial acetic acid containing 3.0 ml of methanethiol. After 45 minutes, the solution is diluted with chloroform and added to water. The chloroform solution is washed with water, a saturated sodium bicarbonate solution and water, dried (MgSO₄ anh.) and evaporated to a gummy residue. This is chromatographed on a column of silica gel (50 g), eluting the column successively with chloroform-hexane, chloroform and chloroform-ethyl acetate mixtures (9:1 and 8:2) to afford successively the over-reacted steroid (~500 mg), the title compound (4.0 g) and unreacted starting steroid (2.0 g). One crystallization of the 4.0 g material from ethyl acetate-hexane and drying (75° C., 0.3 mm of Hg, 5.0 hours) affords the analytical specimen of the title compound as colorless crystals (3.6 g), melting point 203°–204° C. dec. with consistent spectral data.

Anal. Calc'd. for $C_{21}H_{30}O_2S_2$: C, 66.61; H, 7.99; S, 16.90; Found: C, 66.72; H, 7.96; S, 17.06.

EXAMPLE 17

17α-(Ethylthio)-11β-hydroxy-17-(methylthio)-androsta-1,4-dien-3-one (A)

11β-Hydroxy-17-(methylthio)androsta-1,4,16-triene-3-one

A suspension of 11β-hydroxy-17,17-bis-(methylthio)androsta-1,4-diene-3-one (2.6 g) in dry diethylbenzene (120 ml) is refluxed for 1.0 hour in a bath at about 200° C. The resulting solution is then cooled to room temperature and subsequently in an ice bath to afford the title compound as needles (2.1 g), after filtration and washing with hexane. The filtrate is subsequently chromatographed on a column of silica gel (30 g) to afford another 100 mg of product. The total yield is thus 2.2 g of product, melting point 240°–241° C., dec., with a consistent nmr spectrum.

(B)

17α-(Ethylthio)-11β-hydroxy-17-(methylthio)-androsta-1,4-diene-3-one

A suspension of 11β-hydroxy-17-(methylthio)-androsta-1,4,16-triene-3-one (1.0 g) in dichloromethane (70 ml) containing ethanethiol (1.12 g; 1.36 ml) is cooled and stirred in a bath at −78° C. (acetone-dry ice) and boron trifluoride etherate (860 mg; 0.76 ml) is added. After 2.0 hours, the reaction is quenched by the addition of a solution of sodium hydroxide (2.0 g) in methanol-water (1:1; 30 ml) under vigorous stirring. The mixture is then warmed to room temperature, diluted with 20% hydrochloric acid (50 ml) and extracted with chloroform. The chloroform solution is washed with a dilute sodium bicarbonate solution and water, dried (MgSO4 anhydrous), evaporated and the residue is chromatographed on a column of silica gel (20 g) eluting with chloroform and chloroformethyl acetate (9:1) to remove some 17-ketone that is present. The title compound obtained (1.03 g) is crystallized from ethyl acetatehexane and dried (75° C., 0.3 mm of Hg, 7.0 hours) to afford the analytical specimen of the title compound (850 mg), melting point 176°–178° C., with consistent spectral data.

Anal. Calc'd. for $C_{22}H_{32}O_2S_2$: C, 67.30; H, 8.22; S, 16.33; Found: C, 67.54; H, 7.92; S, 16.26.

EXAMPLE 18

17β-(Ethylthio)-11β-hydroxy-17-(methylthio)-androsta-1,4-dien-3-one (A)

17-(Ethylthio)-11β-hydroxyandrosta-1,4,16-trien-3-one

A suspension of 4.4 g of 17,17-bis(ethylthio)-11β-hydroxyandrosta-1,4-dien-3-one (see example 2) in 100 ml of dry diethyl benzene is stirred at 190°–195° C. (oil bath temperature) for 1.5 hours. The suspension becomes a solution during the heating; the resulting solution is cooled to 0° C. The solid that precipitates is filtered and dried in vacuo to give 3.0 g of the title compound, melting point 216°–218° C., with consistent spectral data.

The filtrate is chromatographed on a 50-gram silica gel column, eluting successively with 1:1 chloroform-hexane and 9:1 chloroformethyl acetate to give 0.5 g more of the title compound.

(B)

17β-(Ethylthio)-11β-hydroxy-17-(methylthio)-androsta-1,4-dien-3-one

A suspension of 1.0 g of 17-(ethylthio)-11β-hydroxyandrosta-1,4,16-trien-3-one in 30 ml of dry dichloromethane and 1.5 ml of a solution of methyl mercaptan in dry dichloromethane (1.34 g in 10 ml of dry dichloromethane) is cooled to about −78° C. (dry ice-acetone bath) under nitrogen. Boron trifluoride etherate (0.4 ml) is then added and the suspension gradually becomes a solution. The solution is stirred at −78° C. under nitrogen for 5 hours, quenched with 5 ml of a solution of sodium hydroxide in methanol (2.0 g of sodium hydroxide in 40 ml of methanol) at about −70° C. under vigorous stirring, diluted with chloroform and poured into water. The chloroform solution is separated, dried over anhydrous $Na_2SO_4$ and evaporated in vacuo to give 1.1 g of a foamy solid. A small scale run using 100 mg of 17-(ethylthio)-11β-hydroxyandrosta-1,4,16-trien-3-one gives 100 mg of material identical in tlc and NMR. These two are combined, dissolved in chloroform and chromatographed on a 25-gram silica gel column, eluting successively with chloroform and 5:95 ethyl acetate-chloroform to give 1.05 g of the title compound. Crystallization from acetone-hexane gives 850 mg of an analytical specimen, melting point 208°–210° C., with consistent spectral data.

Anal. Calc'd for $C_{22}H_{32}O_2S_2$: C, 67.30; H, 8.22; S, 16.33; Found: C, 67.42; H, 8.36; S, 16.34.

EXAMPLES 19–24

Following the procedure of example 2, but substituting the steroid listed in column I for 11β-hydroxyandrosta-1,4-diene-3,17-dione and the thiol listed in column II for ethanethiol, yields the steroid listed in column III.

| | Column I | Column II | Column III |
|---|---|---|---|
| 19. | 9-Fluoro-11β-hydroxy-androsta-1,4-diene-3,17-dione | cyclohexanethiol | 17,17-bis(cyclohexylthio)-9-fluoro-11β-hydroxyandrosta-1,4-diene-3-one |
| 20. | 9-Fluoro-11β-hydroxy-androsta-1,4,6-triene-3,17-dione | ethanethiol | 17,17-bis(Ethylthio)-9-fluoro-11β-hydroxyandrosta-1,4,6-triene-3-one |
| 21. | 6α,9α-Difluoro-11β-hydroxyandrosta-1,4-diene-3,17-dione | methanethiol | 6α,9α-Diflouro-11β-hydroxy-17,17-bis(methylthio)androsta-1,4-diene-3-one |
| 22. | 9-Fluoro-11β-hydroxy- | propanethiol | 9-Fluoro-11β-hydroxy-6α- |

| | Column I | Column II | Column III |
|---|---|---|---|
| | 6α-methyl-androsta-1,4-diene-3,17-dione | | methyl-17,17-bis(propylthio)-androsta-1,4-diene-3-one |
| 23. | 9-Fluoro-11β,16α-dihydroxy-androsta-1,4-diene,3,17-dione | methanethiol | 9-Fluoro-11β,16α-dihydroxy-17,17-bis(methylthio)androsta-1,4-diene-3,17-dione |
| 24. | 9-Fluoro-11β-hydroxyandrosta-1,4-diene-3,17-dione | isobutylthiol | 9-Fluoro-11β-hydroxy-17,17 bis[(isobutyl)thio]androsta-1,4-diene-3,17-dione |

What is claimed is:

1. A 3-ketoandrostene having in the 17-position the substituents $R_1$-S- and $R_2$-S- wherein $R_1$ and $R_2$ are different groups, and each is an alkyl, cycloalkyl or aryl group.

2. A 3-ketoandrostene in accordance with claim 1 having the formula

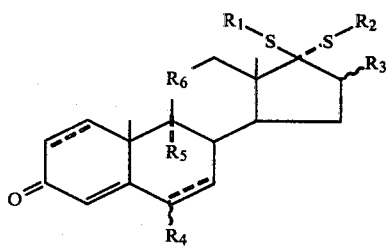

or 1,2-, 6,7- and 15,16-dehydro derivatives thereof, wherein $R_1$ and $R_2$ are different alkyl, cycloalkyl or aryl groups;

$R_3$ is hydrogen, hydroxy, alkoxy, aryloxy, alkylthio, arylthio,

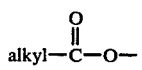

or halogen;

$R_4$ is hydrogen, methyl, hydroxy,

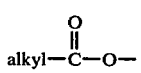

or halogen;

$R_5$ is hydrogen or halogen; and $R_6$ is carbonyl or β-hydroxymethylene.

3. A 3-ketoandrostene in accordance with claim 2 wherein $R_4$ is hydrogen.

4. A 3-ketoandrostene in accordance with claim 2 wherein $R_5$ is fluorine.

5. A 3-ketoandrostene in accordance with claim 2 wherein $R_6$ is β-hydroxymethylene.

6. A 3-ketoandrostene having the formula

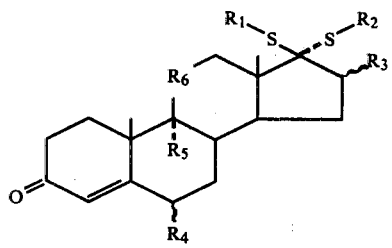

or 1,2-, 6,7- and 15,16-dehydro derivatives thereof, wherein $R_1$ and $R_2$ are the same alkyl, cycloalkyl or aryl group;

$R_3$ is hydroxy, alkoxy, aryloxy, alkylthio, arylthio,

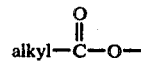

or halogen;

$R_4$ is hydrogen, methyl, hydroxy,

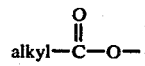

or halogen;

$R_5$ is hydrogen or halogen; and $R_6$ is carbonyl or β-hydroxymethylene.

7. A 3-ketoandrostene in accordance with claim 6 wherein $R_4$ is hydrogen.

8. A 3-ketoandrostene in accordance with claim 6 wherein $R_5$ is fluorine.

9. A 3-ketoandrostene in accordance with claim 6 wherein $R_6$ is β-hydroxymethylene.

10. The 3-ketoandrostene in accordance with claim 6, (11β,16α)-17,17-bis(ethylthio)-9-fluoro-11-hydroxy-16-methoxyandrosta-1,4-dien-3-one.

11. The 3-ketoandrostene in accordance with claim 2, 17-(ethylthio)-9-fluoro-11β-hydroxy-17-(methylthio)androsta-1,4-dien-3-one.

12. The 3-ketoandrostene in accordance with claim 2, 17-(ethylthio)-9-fluoro-11β-hydroxy-17-(phenylthio)androsta-1,4-dien-3-one.

13. The 3-ketoandrostene in accordance with claim 2, 17-(butylthio)-17-(ethylthio)-9-fluoro-11β-hydroxyandrosta-1,4-dien-3-one.

14. The 3-ketoandrostene in accordance with claim 2, 17α-(ethylthio)-9-fluoro-11β-hydroxy-17-(methylthio)androsta-1,4-dien-3-one.

15. The 3-ketoandrostene in accordance with claim 2, 17β-(ethylthio)-9-fluoro-11β-hydroxy-17-(methylthio)androsta-1,4-dien-3-one.

16. The 3-ketoandrostene in accordance with claim 2, 17α-(ethylthio)-11β-hydroxy-17-(methylthio)androsta-1,4-dien-3-one.

17. The 3-ketoandrostene in accordance with claim 2, 17β-(ethylthio)-11β-hydroxy-17-(methylthio)androsta-1,4-dien-3-one.

18. A method of treating topical inflammation in a mammalian host comprising topically administering an effective amount of a 3-ketoandrostene having in the 17-position the substituents $R_1$-S- and $R_2$-S- wherein $R_1$ and $R_2$ are the same or different and each is alkyl, cycloalkyl or aryl.

19. A method in accordance with claim 18 wherein the 3-ketoandrostene has the formula

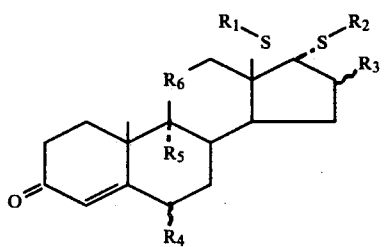

or 1,2-, 6,7- and 15,16-dehydro derivatives thereof, wherein $R_1$ and $R_2$ are the same or different alkyl, cycloalkyl or aryl groups;

$R_3$ is hydrogen, hydroxy, alkoxy, aryloxy, alkylthio, arylthio,

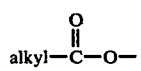

or halogen;

$R_4$ is hydrogen, methyl, hydroxy,

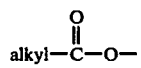

or halogen;

$R_5$ is hydrogen or halogen; and $R_6$ is carbonyl or β-hydroxymethylene.

20. A method in accordance with claim 19 wherein $R_4$ is hydrogen.

21. A method in accordance with claim 19 wherein $R_5$ is fluorine.

22. A method in accordance with claim 19 wherein $R_6$ is β-hydroxymethylene.

23. A process for preparing a steroid having the formula

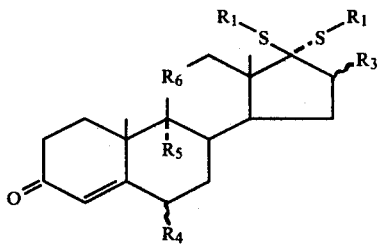

or 1,2- and 6,7-dehydro derivatives thereof, which comprises reacting a steroid having the formula

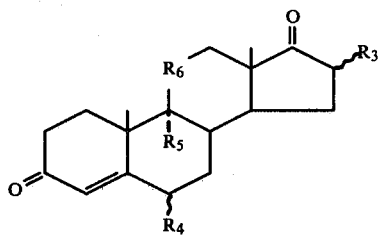

or 1,2- and 6,7-dehydro derivatives thereof with a thiol having the formula $R_1$-SH in the presence of a Lewis acid and in the presence of a dimethylformamide dialkyl acetal; wherein $R_1$ is alkyl, cycloalkyl or aryl, $R_3$ is hydrogen, hydroxy, alkoxy, aryloxy, alkylthio, arylthio,

or halogen, $R_4$ is hydrogen, methyl, hydroxy,

or halogen, and $R_5$ is hydrogen or halogen, and $R_6$ is carbonyl or β-hydroxymethylene.

24. A process in accordance with claim 23 wherein the dimethylformamide dialkyl acetal is dimethylformamide dimethyl acetal.

* * * * *